United States Patent [19]

Schenk, Jr. et al.

[11] Patent Number: 4,810,988

[45] Date of Patent: Mar. 7, 1989

[54] SLAG DETECTOR TRANSDUCER COIL ASSEMBLY

[75] Inventors: Harold L. Schenk, Jr.; Donald T. Beecher, both of Murrysville, Pa.

[73] Assignee: Westinghouse Electric Corp., Pittsburgh, Pa.

[21] Appl. No.: 208,711

[22] Filed: Jun. 20, 1988

[51] Int. Cl.4 .............................................. H01F 27/08
[52] U.S. Cl. ...................................... 336/60; 324/224; 336/197
[58] Field of Search .................. 324/204, 224; 336/55, 336/57, 58, 59, 60, 197

[56] References Cited

U.S. PATENT DOCUMENTS

| | | | |
|---|---|---|---|
| 3,152,303 | 10/1964 | Lary et al. | 324/224 X |
| 3,456,715 | 7/1969 | Freedman et al. | 164/155 |
| 4,173,299 | 11/1979 | Kollberg et al. | 324/204 X |
| 4,352,078 | 9/1982 | Moore | 336/60 |
| 4,523,146 | 6/1985 | Champaigne | 324/204 |
| 4,529,029 | 7/1985 | Block | 324/204 X |
| 4,590,424 | 5/1986 | Girot et al. | 324/204 |
| 4,635,832 | 1/1987 | Angerer et al. | 324/204 X |

FOREIGN PATENT DOCUMENTS 52-29800 of 0000 Japan.
55-97846 of 0000 Japan.
57-56154 of 0000 Japan.
609595 of 0000 Switzerland.

Primary Examiner—Thomas J. Kozma
Attorney, Agent, or Firm—M. J. Moran

[57] ABSTRACT

A compressed-air cooled transducer coil assembly for slag detector apparatus includes a refractory shield, top and bottom end blocks, a coil winding, and at least two spaced-apart guide bars. The shield may be positioned to coaxially surround the pour tube of a continuous steel caster so as to leave a space therebetween. The end pieces are connected to the shield. The coil winding is connected to the end blocks and is positioned so as to coaxially surround the shield leaving an air gap therebetween. The guide bars each have a bore whose lower end is attached to the bottom end block and whose middle portion projects into the space between the shield and the pour tube. The top and bottom end blocks have conduits which communicate with the air gap and the bores.

4 Claims, 3 Drawing Sheets

SLAG DETECTOR TRANSDUCER COIL ASSEMBLY

CROSS REFERENCE TO RELATED APPLICATIONS

Reference is hereby made to the following copending applications dealing with related subject matter and assigned to the assignee of the present invention:

1. "Slag Detector Apparatus for Molten Steel Process Control" by George T. Hummert et al., assigned U.S. Ser. No. 07/094,983 and filed Sept. 9, 1987.
2. "Improved Discrete Excitation Coil Producing Seal at Continuous Casting Machine Pouring Tube Outlet Nozzle/Mold Inlet Interface" by Dennis Pavlik et al., assigned U.S. Ser. No. 050,272 and filed May 15, 1987.
3. "Liquid Metal Electromagnetic Flow Control Device Incorporating a Pumping Action" by Robert M. Del Vecchio et al., assigned U.S. Ser. No. 070,017 and filed July 6, 1987.

BACKGROUND OF THE INVENTION

1. Field of the Invention

The present invention relates generally to detecting slag in a stream of molten steel or the like and, more particularly, is concerned with the design of the slag detector transducer coil assembly.

2. Description of the Prior Art

In the continuous casting of steel billets, blooms, and slabs, steel is transferred from a ladle to a tundish in a continuous stream via gravity feed through a refractory shroud. A valve in the bottom of the ladle is used to terminate the steel flow as the ladle empties and another ladle is brought into position to keep the tundish replenished with molten steel. Each ladle of molten steel is referred to as a "heat", and many heats are required for one continuous casting run. In order to maintain high quality and a uniform cast product, it is important to maintain a uniform quality of molten steel in the succession of heats.

Slag, which consists of various oxides created in the furnace and ladle, has a lower density than steel and consequently floats on the steel surface. Since steel is withdrawn from the ladle's bottom, slag is kept from contaminating the tundish and the finished product. This technique works until near the end of each heat, when slag tends to mix with steel due to vortexing effects created by the steel discharge. In order to minimize contamination, the level of steel in the ladle is monitored visually and the flow is terminated when it appears to be near the onset of vortexing; i.e., slag entrainment, in the discharge stream.

Usually, the flow is terminated early, and valuable steel is subsequently scrapped along with slag for recycling in the furnace. Occasionally flow is not terminated in time, and large volumes of slag are sucked into the discharge and into the tundish. Since there is no reliable means available for measuring slag content in the discharge stream, the process is strictly a matter of judgement based upon experience, and the tendency is to maintain quality of the finished product by cutting flow of uncontaminated steel. For a typical slab caster, the net worth of disposed steel from each heat is worth several hundred-thousand to several million dollars annually.

Novel means for detecting the onset of slag entrainment by using a transducer coil which is mounted coaxially with the shroud transferring the molten steel discharge from the ladle to the tundish are disclosed in U.S. Patent Nos. 4,523,146; 4,590,424 and 4,635,832. But prior art structures and methods for detecting slag in molten metal with a coil during pouring of the metal have not dealt with a dependable and durable coil construction.

A transducer coil which is mounted co-axially with the molten steel discharge stream flowing through a refractory shroud is used to detect the onset of slag entrainment in the steel stream. Since the temperature of the outer surface of the shroud can reach at least 1300° F., and it is desirous to construct the coil as compactly as possible to keep its resistance low, it becomes imperative to design the coil assembly to minimize its temperature environment. The necessity for minimizing the coil temperature is two-fold, firstly, to keep its resistance low since the principal of the slag detection scheme depends upon the measurement of the percentage change of the coil resistance, and secondly, so that the coil winding insulation can survive during the lifetime of the slag detector assembly.

SUMMARY OF THE INVENTION

It is an object of the invention to provide a slag-detector transducer coil assembly which is self-protected against heat damage from contact with a hot pour tube during tube removal.

It is another object of the invention to provide such a coil assembly design having enhanced cooling to increase operating life.

To achieve the foregoing and other objects and in accordance with the purpose of the present invention as embodied and broadly described herein, the transducer coil assembly, for use in apparatus which detects the presence of slag within a pour tube, includes a heat-resistant shield, top and bottom end pieces, a coil winding, and at least two guide bars. The heat-resistant shield may be positioned to coaxially surround a portion of the pour tube leaving a space between the shield and the tube. The top end piece is connected to the top end of the shield and the bottom end piece is connected to the bottom end of the shield. The coil winding is positioned to coaxially surround the shield leaving an air gap between the winding and the shield, with the upper terminus of the coil winding attached to the top end piece and lower terminus of the coil winding attached to the bottom end piece. Each guide bar has a bore with an upper part and a lower part, an upper end, and a lower end. The lower end is attached to the bottom end piece. Each guide bar also has a middle portion which projects into the space between the pour tube and the shield. The top end piece has a top conduit with a first end in communication with the air gap top portion, and a second end which defines a compressed air inlet. The bottom end piece has a bottom conduit with a first terminus in communication with the air gap bottom portion and a second terminus in communication with bottom part of the bore. The top part of the bore has an air exhaust.

Several benefits and advantages are derived from the invention. The internally-cooled hollow guide bars make the slag-detector transducer coil assembly self-protecting against heat damage from contact with a hot pour tube during tube removal. The compressed air flowing through the air gap between the coil winding and the shield and through the top and bottom conduits of the top and bottom end pieces provide better cooling to the transducer coil assembly for longer life.

DESCRIPTION OF THE PREFERRED EMBODIMENTS

Figure 1:
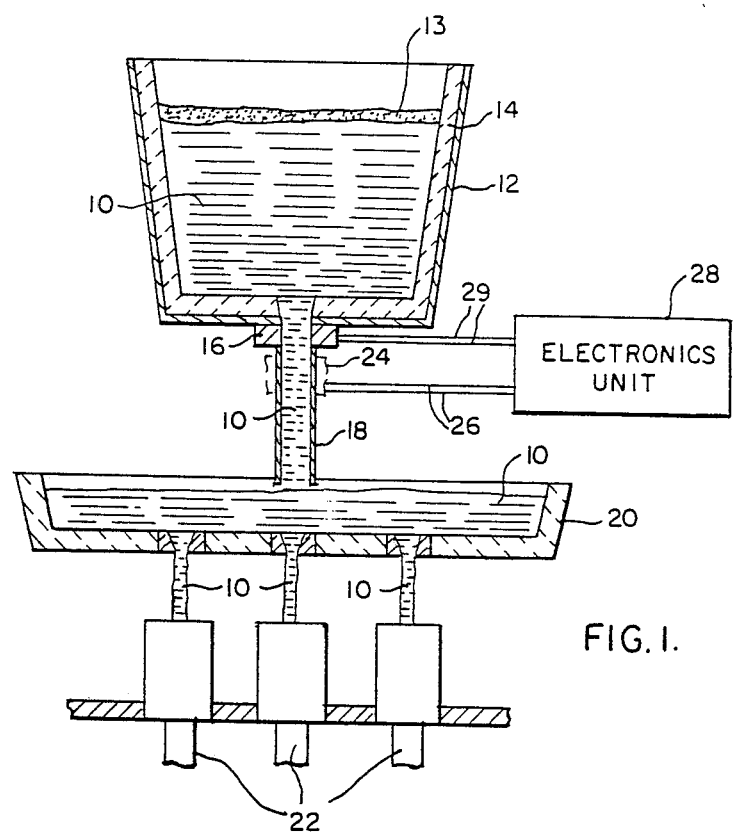
FIG. 1 is a schematic diagram of a continuous caster of prior art construction and including in addition the slag-detector transducer coil assembly of this invention.
Figure 2:
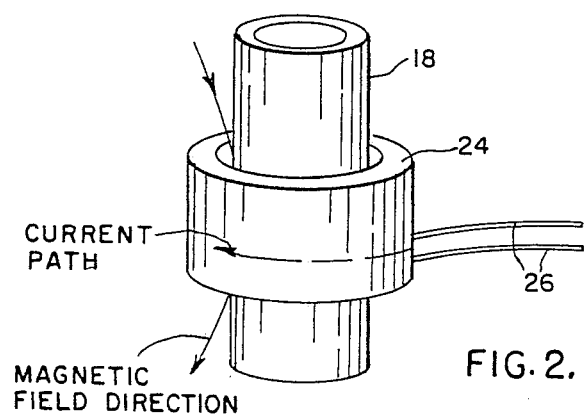
FIG. 2 is a perspective and schematic view of the transducer coil assembly and a portion of the pour tube of FIG. 1.

In FIGS. 1 and 2, molten steel 10 in a ladle 12, having a refractory liner 14, passes through a valve 16 into a pour tube 18. A layer of liquid slag 13, having a specific gravity less than that of the molten steel 10, floats on the surface of the molten steel contained in the ladle. The slag 13 forms an insulative layer that helps maintain the superheat temperature of the molten steel.

From the pour tube 18, the molten metal enters a tundish 20 and then into separate molds 22 for the production of cast steel. Surrounding the pour tube 18 is a transducer coil assembly 24 of the present invention. Insulated leads 26 from the coil assembly (FIG. 2) enter an electronics unit 28 which together with the coil assembly define the slag detector. Electromagnetic slag detectors are known in the prior art, and the electronics unit does not form a part of the present invention. An output lead 29 from the electronics unit is used to close the valve 16 when slag is detected.

Figure 3:
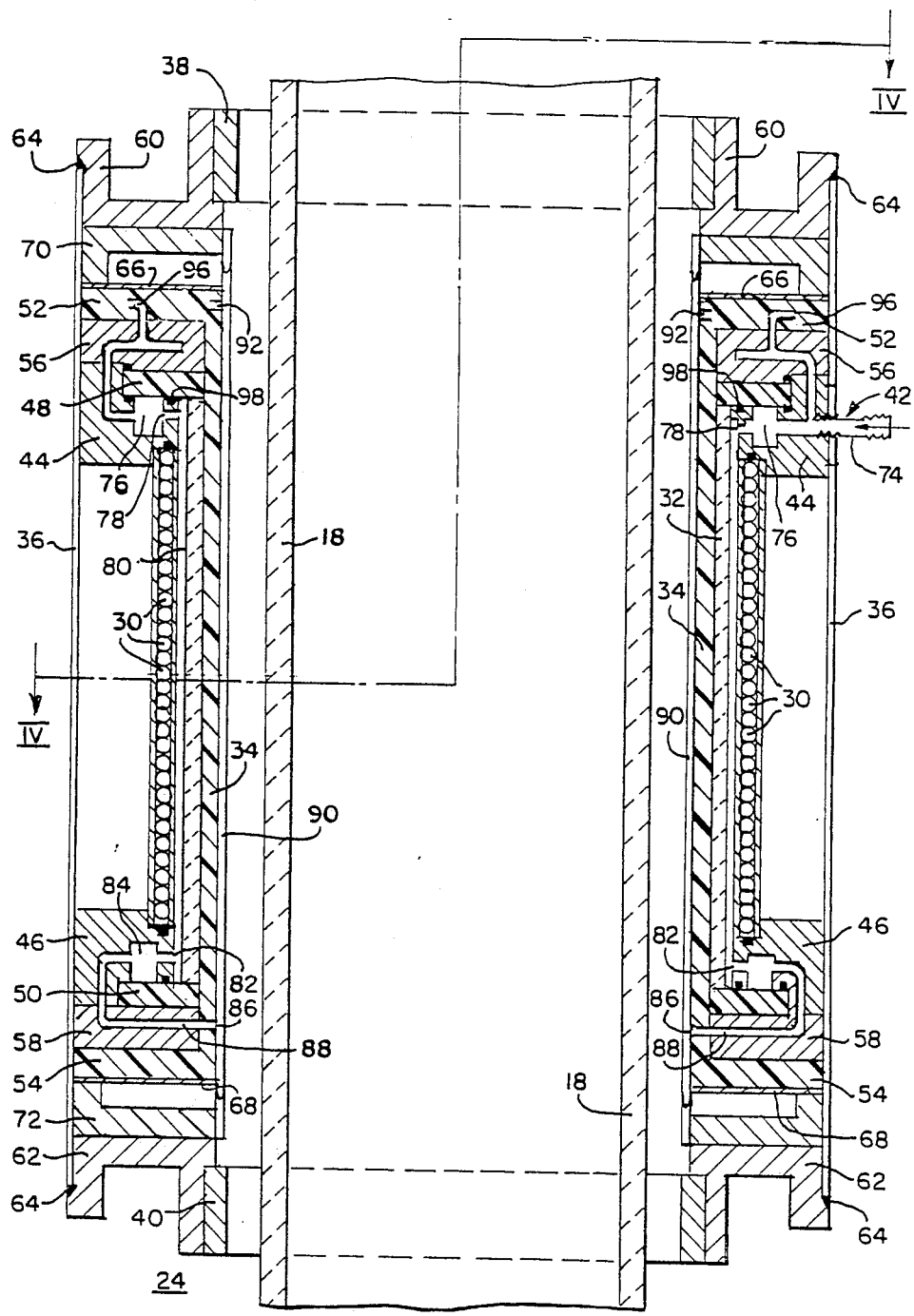
FIG. 3 is a longitudinal sectional view of the transducer coil assembly and pour tube section of FIG. 2.

In accordance with this invention the transducer coil assembly 24 (FIG. 3) comprises a coil 30, a refractory shield 32, an insulating sleeve 34, outer support bars 36, upper and lower annular collars 38, 40, and a cooling system generally indicated at 42. The coil 30, the refractory shield 32, and the insulating sleeve 34 are cylindrical members concentrically disposed about the pour tube 18. The coil 30 comprises electrical windings of a conventional construction and extends between upper and lower coil supports 44, 46, which are annular and composed of a dielectric material such as plastic.

Figure 4:
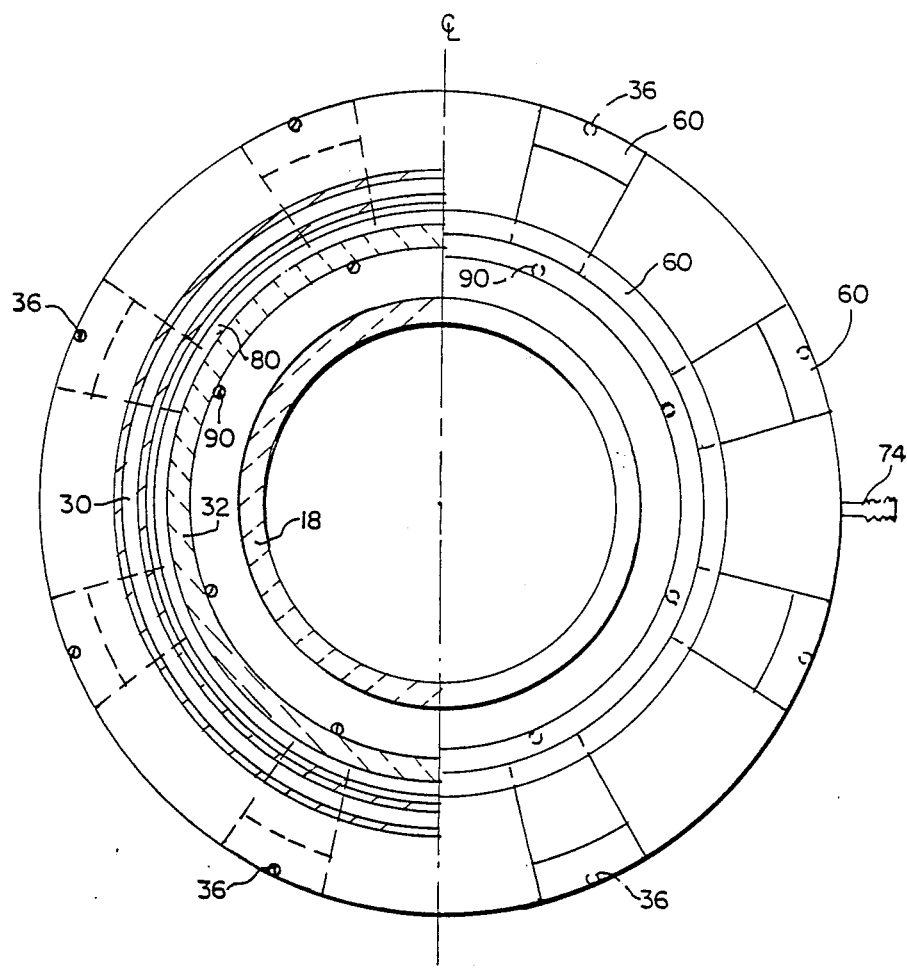
FIG. 4 is a transverse sectional view taken on the line IV—IV of FIG. 3.

The refractory shield 32 which is concentrically disposed (FIG. 4) within the coil 30, is located between upper and lower shield rings 48, 50 which are likewise composed of a dielectric material, such as lava, and which are disposed between the corresponding and lower coil supports 44, 46. The insulating sleeve 34 extends between upper and lower insulating sleeves 52, 54 where the sleeves are supported adjacent to upper and lower support and cooling collars 56, 58. In the alternative, the insulating sleeve 34 and the sleeves 52, 54 may be integral members composed of a glass epoxy material.

The collar 56 is disposed between the insulating sleeve 52 and the upper coil support 44. Similarly, the collar 58 is disposed between the insulating sleeve 54 and the lower coil support 46. The upper and lower support collars 56, 58 are preferably composed of a metal having a high coefficient of thermal conductivity, such as copper.

In addition to the foregoing, the transducer coil assembly 24 comprises support means for holding the assembly of the several parts 30, 32, 34, 44, 46, 48, 50–58 together against longitudinal separation of the axis of the port tube 18. For that purpose, the plurality of outer support bars 36, such as eight bars, extend between upper and lower bar blocks 60, 62, one for each bar 36 at each end thereof and to which the end portions of each bar are secured such as by a weld 64.

The insulating sleeves 52, 54 are retained in place against the surface of the upper and lower support and cooling collars 56, 58, respectively by annular disks 66, 68 where they are retained by disk supports 70, 72 which, in turn, are in surface to surface abutment with the corresponding upper and lower bar blocks 60, 62. Accordingly, with the eight peripherally spaced outer support bars 36 retained intention between the upper and lower bar blocks 60, 62 the assembly of the several parts are retained in snug fitting positions with respect to each other. Also, spaced-apart splash guard plates can coaxially surround coil 30.

The cooling system 42, comprises a fluid inlet 74 which communicates with a plurality of passages including a manifold 76 connecting by a plurality of peripherally spaced inlets 78 to an annular chamber 80 which is disposed between the coil 30 and the refractory shield 32. The upper end of the chamber 80 extends from the several spaced inlets 78 downwardly to corresponding outlets 82 leading to a plenum chamber 84. The plenum chamber 84 is located in the lower coil support 46 and includes peripherally spaced outlets 86 which by passages 88 in the lower support and cooling collar 58 lead to peripherally spaced elongated guide tubes 90. The upper ends of the several guide tubes 90 for conducting coolant fluid include outlets 92, which exhaust into the insulating sleeve 52. From where the coolant gas exhausts into the surrounding atmosphere.

The cooling system also includes peripherally spaced outlets leading from the upper plenar chambers 76 in the coil support 44 to a connecting passage or conduit 94 from where the coolant gas enters the upper support and cooling collars and is then exhausted by the peripherally spaced outlets 96, which, like the outlets 92 exhaust into the insulating sleeve 52.

The coolant system 42 provides means for circulating a gas coolant, such as air, nitrogen, or an inert gas, throughout the transducer coil assembly 24 for maintaining the coil 30 and associated parts at the necessary operating temperature. A leak free cooling system is insured by the use of suitable seals such as O-rings 98 at each of the coil assemblies during assembly of the coil assembly 24 when the upper ends of the outer support bars are secured in place such as by the welds 64. The dimensions of the plenum chambers and of the radial flow holes are such that air entering the upper plenum chamber at 46 psia and 100° F. and discharging from the lower plenum chamber at 100° F. will remove 10,000 Btu/hour. Three chromel-alumel thermocouples (not shown) are embedded in the coil winding 30 for monitoring the winding temperature.

Accordingly, the air cooled transducer coil provides means for detecting the onset of slag entrapment in a stream of molten metal, usually steel. Since the coil is a coaxial winding surrounding the ladle shroud containing the metal, it is protected from the high temperature environment by refractory shields, and in addition, by an air cooling system by virtue of its special design. By maintaining a cool winding coil, the coil resistance is low which is imperative as the detection scheme depends upon the measurement of the percentage change in the coil resistance. Finally, since the winding coil can be maintained at a reasonably constant temperature, the effect of small changes in slag content in the molten stream are less likely to be masked by variations in the winding coil temperature.

What is claimed is:

1. A transducer coil assembly, for use in apparatus which detects the presence of slag within a pour tube, said assembly comprising:
   (a) a refractory shield disposable to coaxially surround a portion of the pour tube leaving a space therebetween, said shield including a top and bottom end;
   (b) a top end block connected to the top end of said shield and a bottom end block connected to the bottom end of said shield;
   (c) a coil winding disposed to coaxially surround said shield leaving an air gap therebetween, wherein said air gap has a top portion and a bottom portion, with said coil winding having an upper terminus attached to said top end block and having a lower terminus attached to said bottom end block; and
   (d) a plurality of spaced-apart guide bars, each guide bar having a bore with an upper part and a lower part, an upper end, a lower end attached to said bottom end block, and a middle portion projecting into said space and connected to the upper and lower ends,
   wherein said top end block has a top conduit with a first end communicating with the top portion of said air gap and a second end defining a compressed air inlet, wherein said bottom end block has a bottom conduit with a first terminus communicating with the bottom portion of said air gap and a second terminus communicating with the lower part of said bores and wherein said upper part of said bores has an air exhaust.

2. The transducer coil assembly of claim 1, wherein said refractory shield and said coil winding each have a generally right circular cylindrical shape.

3. The transducer coil assembly of claim 1 also including spaced-apart splash guard plates disposed to coaxially surround said winding.

4. The transducer coil assembly of claim 3, wherein said refractory shield and said coil winding each have a generally right circular cylindrical shape.

* * * * *